(12) United States Patent
Elder et al.

(10) Patent No.: US 12,161,533 B2
(45) Date of Patent: Dec. 10, 2024

(54) NEGATIVE PRESSURE WOUND THERAPY DRESSING RECOGNITION, WOUND STATUS DETECTION, AND THERAPY ADJUSTMENT

(71) Applicant: T.J.Smith and Nephew, Limited, Hull (GB)

(72) Inventors: David Michael Elder, Inverness (GB); Hannah Bailey Weedon, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 77 days.

(21) Appl. No.: 17/977,220

(22) Filed: Oct. 31, 2022

(65) Prior Publication Data

US 2023/0105262 A1 Apr. 6, 2023

Related U.S. Application Data

(63) Continuation of application No. 16/919,684, filed on Jul. 2, 2020, now Pat. No. 11,484,640.

(30) Foreign Application Priority Data

Jul. 3, 2019 (GB) ...................................... 1909551
Nov. 14, 2019 (GB) ...................................... 1916553

(51) Int. Cl.
*A61F 13/05* (2024.01)
*A61M 1/00* (2006.01)

(52) U.S. Cl.
CPC .............. *A61F 13/05* (2024.01); *A61M 1/962* (2021.05); *A61M 1/966* (2021.05);
(Continued)

(58) Field of Classification Search
CPC ........ A61M 1/60–684; A61M 1/71–75; A61M 1/77–82; A61M 1/90–985;
(Continued)

(56) References Cited

U.S. PATENT DOCUMENTS 10,086,117 B2 10/2018 Locke et al.
10,940,243 B2 3/2021 Hall et al.
(Continued)

FOREIGN PATENT DOCUMENTS

CN 107714295 A 2/2018
EP 3009946 A1 4/2016
(Continued)

OTHER PUBLICATIONS

Bon, M., "A Basic Introduction to BLE Security," retrieved from https://www.digikey.com/eewiki/display/Wireless/A+Basic+Introduction+to+BLE+Security, Oct. 25, 2016, 5 pages.
(Continued)

*Primary Examiner* — Sarah Al Hashimi
*Assistant Examiner* — Hans Kaliher
(74) *Attorney, Agent, or Firm* — Knobbe, Martens, Olson & Bear, LLP

(57) ABSTRACT

Negative pressure wound therapy systems, apparatuses, and methods for operating the systems and apparatuses are disclosed. In some cases, the system can include a dressing having electronic circuitry that wirelessly communicates a dressing identifier and/or other dressing information to a controller of a pump assembly of the system. The controller can automatically modify one or more operational parameters of the pump assembly based on the dressing identifier and/or other dressing information wirelessly communicated. Duration of time over which the dressing has been in use can be monitored and provision of therapy by the pump assembly can be disabled responsive to a determination that the duration of time has reached operational lifetime of the dressing.

19 Claims, 6 Drawing Sheets

(52) U.S. Cl.
CPC . *A61M 2205/18* (2013.01); *A61M 2205/3334* (2013.01); *A61M 2205/3553* (2013.01); *A61M 2205/52* (2013.01); *A61M 2205/581* (2013.01); *A61M 2205/582* (2013.01); *A61M 2205/583* (2013.01)

(58) Field of Classification Search
CPC ...... A61M 2205/582; A61M 2205/583; A61M 2205/3344; A61M 2205/6018; A61F 13/0216; A61F 13/00068
See application file for complete search history.

(56) References Cited

U.S. PATENT DOCUMENTS

| | | | |
|---|---|---|---|
| 10,959,884 B2 | 3/2021 | Rapp | |
| 11,058,807 B2 | 7/2021 | Weston | |
| 2003/0119568 A1 | 6/2003 | Menard | |
| 2008/0300578 A1 | 12/2008 | Freedman | |
| 2010/0022990 A1* | 1/2010 | Karpowicz | A61M 1/74 604/543 |
| 2012/0109034 A1 | 5/2012 | Locke et al. | |
| 2012/0136325 A1* | 5/2012 | Allen | A61M 5/48 604/319 |
| 2014/0005618 A1 | 1/2014 | Locke et al. | |
| 2014/0235166 A1 | 8/2014 | Molettiere et al. | |
| 2015/0011970 A1 | 1/2015 | Kamen et al. | |
| 2015/0223278 A1 | 8/2015 | Reaston et al. | |
| 2016/0261974 A1 | 9/2016 | Arrizza | |
| 2017/0239412 A1 | 8/2017 | Court | |
| 2018/0060529 A1 | 3/2018 | Crothall et al. | |
| 2019/0046697 A1 | 2/2019 | Locke et al. | |
| 2019/0358372 A1 | 11/2019 | Askem et al. | |
| 2020/0306423 A1 | 10/2020 | Tharan et al. | |
| 2020/0330662 A1* | 10/2020 | Hartwell | A61M 1/74 |
| 2021/0077670 A1 | 3/2021 | Long et al. | |
| 2021/0113383 A1 | 4/2021 | Moore et al. | |
| 2021/0128799 A1 | 5/2021 | Askem et al. | |
| 2021/0187171 A1 | 6/2021 | Collinson et al. | |
| 2021/0196869 A1 | 7/2021 | Hartwell et al. | |

FOREIGN PATENT DOCUMENTS

| | | |
|---|---|---|
| EP | 3731888 A2 | 11/2020 |
| WO | WO-2010011920 A2 | 1/2010 |
| WO | WO-2010039481 A1 | 4/2010 |
| WO | WO-2013078095 A2 | 5/2013 |
| WO | WO-2016018448 A1 | 2/2016 |
| WO | WO-2016118330 A1 | 7/2016 |
| WO | WO-2017027850 A1 | 2/2017 |
| WO | WO-2017191149 A1 | 11/2017 |
| WO | WO-2018158250 A1 | 9/2018 |
| WO | WO-2018210693 A1 | 11/2018 |
| WO | WO-2019086475 A1 | 5/2019 |
| WO | WO-2019089118 A1 | 5/2019 |
| WO | WO-2019140444 A1 | 7/2019 |
| WO | WO-2020159677 A1 | 8/2020 |
| WO | WO-2020239781 A1 | 12/2020 |
| WO | WO-2020263508 A1 | 12/2020 |

OTHER PUBLICATIONS

"Data Sheet—LuminOx O2 Sensors—Fluorescence-based Optical Series," SST Sensing Ltd., DS-0030 REV 13, 2017, 2 pages.

* cited by examiner

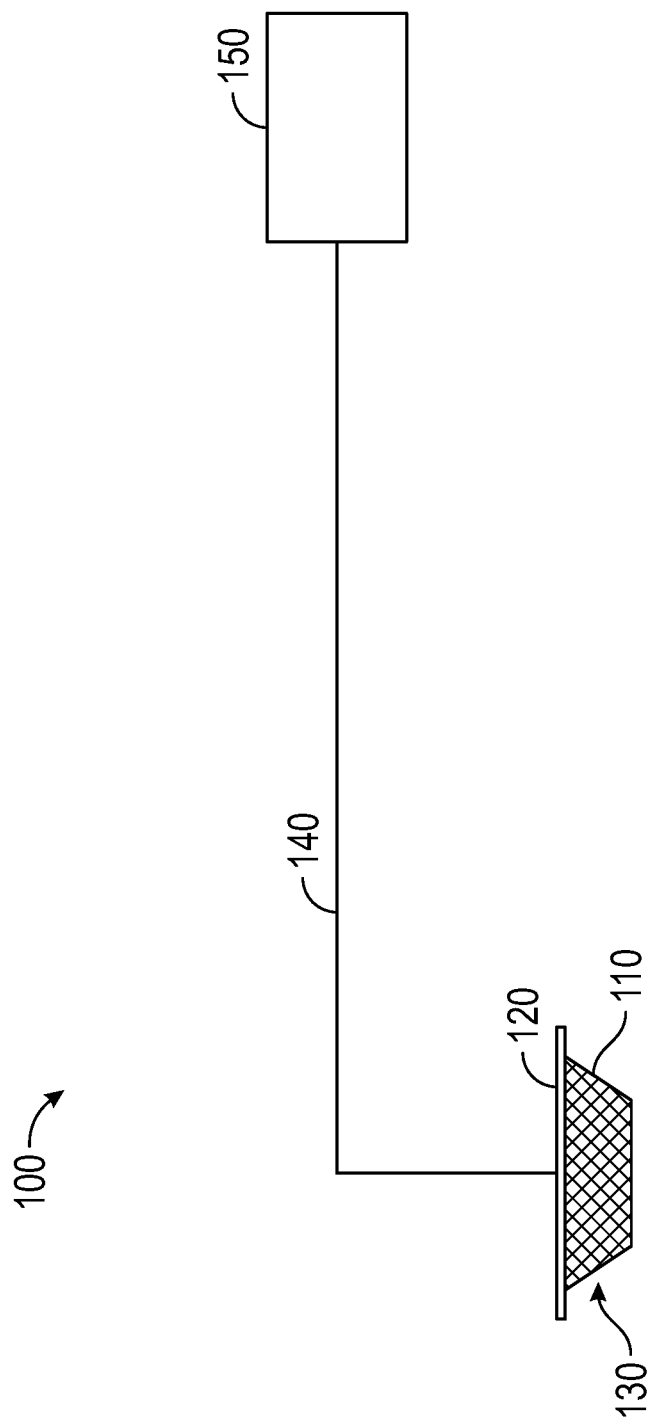

NEGATIVE PRESSURE WOUND THERAPY DRESSING RECOGNITION, WOUND STATUS DETECTION, AND THERAPY ADJUSTMENT

CROSS-REFERENCE TO RELATED APPLICATIONS

This application is a continuation of U.S. patent application Ser. No. 16/919,684, filed on Jul. 2, 2020, which claims priority to United Kingdom Patent Application No. GB 1909551.2, filed on Jul. 3, 2019, and United Kingdom Patent Application No. GB 1916553.9, filed on Nov. 14, 2019, the disclosure of each of which is incorporated by reference in its entirety.

FIELD

Aspects of the present disclosure relate to apparatuses, systems, and methods for the treatment of wounds via negative pressure wound therapy. In some aspects, the present disclosure relates generally to reducing human error in the treatment of wounds with negative pressure wound therapy.

BACKGROUND

Many different types of wound dressings are known for aiding in the healing process of a human or animal. These different types of wound dressings include many different types of materials and layers, for example, pads such as gauze pads or foam pads. Topical negative pressure ("TNP") therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue edema; encouraging blood flow; stimulating the formation of granulation tissue; removing excess exudates, and may reduce bacterial load and thus reduce the potential for infection of the wound. Furthermore, TNP therapy permits less outside disturbance of the wound and promotes more rapid healing. A medical device (e.g., a TNP therapy device) can include a user interface that allows a user to set or control the operation of the medical device. The user interface can be complex, making it difficult for a user to select the correct settings for the operation of the medical device as well as for determining if TNP therapy is delivered correctly. A need exists for simplifying the process by which a user sets or controls the operation of a medical device. A further need exists for reliable detection of the status of TNP therapy.

SUMMARY

Embodiments of the present disclosure relate to apparatuses and methods for wound treatment. Some of the wound treatment apparatuses described herein comprise a pump system or assembly for providing negative pressure to a wound site. The pump assembly can include a source of negative pressure. Wound treatment apparatuses may also comprise wound dressings that may be used in combination with the pump assemblies described herein, and connectors for connecting the wound dressings to the pump assemblies.

Some aspects of the present disclosure are directed to a negative pressure wound therapy system. A negative pressure wound therapy system can include a plurality of wound dressings configured to cover a plurality of wounds. The system can include a plurality of pressure sensors configured to be positioned in a plurality of fluid flow paths fluidically connecting the plurality of wound dressings to a negative pressure wound therapy device. The negative pressure wound therapy device can include a negative pressure source configured to be fluidically connected to the plurality of wound dressings via the plurality of fluid flow paths. The negative pressure source can be configured to aspirate fluid from the plurality of wounds. The negative pressure wound therapy device can include a controller configured to pair with the plurality of pressure sensors. The controller can be configured to provide a first indication of loss of negative pressure in a first wound of the plurality of wounds in response to a determination that a first pressure signal received from a first pressure sensor positioned in a first fluid flow path fluidically connecting the first wound to the negative pressure wound therapy device satisfies a first pressure threshold indicative of a minimum negative pressure level at the first wound.

The system of any of the preceding paragraphs and/or any of the systems disclosed herein can include one or more of the following features. The system can include a plurality of conduits configured to fluidically connect the plurality of wound dressings to the negative wound therapy device. At least one or all pressure sensors of the plurality of pressure sensors can be configured to be positioned on or within a respective conduit of the plurality of conduits. At least one or all conduits of the plurality of conduits can be made from substantially non-rigid material. The controller can be configured to provide a second indication of loss of negative pressure in a second wound of the plurality of wounds in response to a determination that a second pressure signal received from a second pressure sensor positioned in a second fluid flow path fluidically connecting the second wound to the negative pressure wound therapy device satisfies a second pressure threshold indicative of minimum negative pressure level at the second wound. The second wound can be different than the first wound. The second indication can be different than the first indication. The first and second pressure thresholds can be the same.

The system of any of the preceding paragraphs and/or any of the systems disclosed herein can include one or more of the following features. One or more of the first or second indications can include one or more of a visual alarm, audible alarm, tactile alarm, or communication of data to a remote computing device. The system can include a plurality of indicators associated with the plurality of wounds. First indication can include activation of a first indicator of the plurality of indicators to indicate loss of negative pressure in the first wound. First indicator can be associated with the first wound. First indicator can be positioned in a first conduit associated with the first wound dressing. First indicator can be configured to generate a visual indication. First indicator can be positioned at least partially within the first conduit and be at least partially covered by a substantially translucent material. The indicators can be integrated into the pressure sensors.

The system of any of the preceding paragraphs and/or any of the systems disclosed herein can include one or more of the following features. Negative pressure wound therapy device can include an inlet in fluidic communication with the negative pressure source and an additional pressure sensor configured to measure pressure in the inlet. The system can include a connector with a first branch configured to be connected to the inlet and a plurality of second branches configured to be connected to the plurality of fluid flow paths. At least one or all pressure sensors of the plurality of pressure sensors can be configured to wirelessly communicate with the controller. At least one or all indicators if the plurality of indicators can be configured to wirelessly communicate with the controller.

A negative pressure wound therapy system can include a wound dressing, a pump assembly, and a conduit configured to fluidically connect the wound dressing to the pump assembly. The wound dressing can include a sensor. The pump assembly can include a controller and optionally an alarm system. The sensor can be configured to wirelessly communicate a dressing identifier and/or other wound dressing information to the controller. The controller can be configured to automatically adjust one or more operational parameters of the pump based on the dressing identifier and/or the other wound dressing information wirelessly communicated.

The system of any of the preceding paragraphs and/or any of the systems disclosed herein can include one or more of the following features. The sensor can be a pressure sensor. The controller can be configured to automatically adjust an alarm threshold on the alarm system based on the dressing identifier and/or the other wound dressing information wirelessly communicated. The sensor can be adapted to transmit a temperature reading to the controller. The dressing identifier and other wound dressing information can inform the controller of at least one of the pieces of information selected from the group consisting of: a mode of operation of the pump, a size of the dressing, a leak rate of a controlled leak path of the dressing, a contact layer type of the dressing, an optimum negative pressure to apply to the dressing. The sensor can be adapted to inform the controller of a duration that the dressing has been active, or an average pressure, or a flow rate. The dressing can include a controlled leak path. The controller can be configured to lockout operation of the pump assembly based on the dressing identifier and other wound dressing information and on whether the pump assembly detects a canister connected to the pump assembly. The controller can be configured to lockout operation of the pump assembly based on the dressing identifier and other wound dressing information informing the controller that the dressing has been in use for an intended duration of use.

Embodiments or arrangements of the present disclosure are described for illustrative purposes in the context of methods and systems for treating a wound with topical negative pressure (TNP) therapy. However, the present disclosure is not limited to medical devices that are used for TNP therapy and can be applied to medical devices other than medical devices that are used for TNP therapy. The present disclosure can be implemented, for example, in the context of blood glucose monitoring devices, dialysis machines, or other medical devices.

A negative pressure wound therapy system can include at least one wound dressing configured to be positioned over a wound. The at least one wound dressing can include electronic circuitry. The system can include a negative pressure wound therapy device. The device can include a negative pressure source configured to provide negative pressure to the wound. The device can include a controller configured to operate the negative pressure source. The electronic circuitry can be configured to monitor a time duration during which the at least one wound dressing has been in use and communicate to the controller dressing usage information. The controller can be configured to automatically adjust one or more operational parameters of the negative pressure wound therapy device based the dressing usage information.

The system of any of the preceding paragraphs and/or any of the systems disclosed herein can include one or more of the following features. The controller can be configured to, responsive to an indication from the electronic circuitry that the time duration during which the at least one wound dressing has been in use satisfies an operational lifetime of the at least one wound dressing, at least one of disable operation of the negative pressure source or provide a dressing change indication. The electronic circuitry can include a pressure sensor configured to monitor pressure proximal to the wound. The electronic circuitry can be configured to initiate monitoring of the time duration during which the at least one wound dressing has been in use responsive to a determination of at least one of initial activation of the negative pressure source or initial attainment of a threshold negative pressure level proximal to the wound. The determination of the initial attainment of the threshold negative pressure level can be made based on one or more readings of the pressure sensor. The electronic circuitry can be configured to pause monitoring the time duration during which the at least one wound dressing has been in use responsive to receiving an indication from the controller that provision of negative pressure by the negative pressure source has been interrupted. The electronic circuitry can be configured to resume monitoring the time duration during which the at least one wound dressing has been in use responsive to receiving an indication from the controller that provision of negative pressure by the negative pressure source has been resumed.

The system of any of the preceding paragraphs and/or any of the systems disclosed herein can include one or more of the following features. The electronic circuitry can be configured to provide an indication of the time duration during which the at least one wound dressing has been in use. The indication can include at least one of auditory, visual, or tactile indication. The electronic circuitry is configured to provide the indication responsive to a determination that the time duration during which the at least one wound dressing has been in use satisfies a duration threshold, the duration threshold being shorter than an operational lifetime of the at least one wound dressing. The indication can be provided via at least one of the negative pressure wound therapy device or the at least one wound dressing. The electronic circuitry can be configured to communicate to the controller a dressing identifier. The dressing identifier can include at least one of: a mode of operation of the negative pressure source, a size of the at least one wound dressing, a leak rate of a controlled leak of the at least one wound dressing, a wound contact layer type of the at least one wound dressing, an optimum negative pressure to apply to the wound, or an operational lifetime of the at least one wound dressing. The electronic circuitry can include memory configured to store the dressing identifier. The controller can be configured to automatically adjust an alarm threshold based on the dressing identifier. The controller can be configured to disable operation of the negative pressure source based on at least one of: the dressing identifier indicating canisterless operation and responsive to a detection of a canister being fluidically connected to the negative pressure source or the dressing identifier indicating operation with the canister and responsive to a detection of the canister not being fluidically connected to the negative pressure source.

The system of any of the preceding paragraphs and/or any of the systems disclosed herein can include one or more of the following features. The electronic circuitry can be configured to communicate to the controller at least one of an average pressure or a flow rate. The controller can be configured to automatically adjust the one or more operational parameters of the negative pressure wound therapy device based on the at least one of the average pressure or the flow rate. The electronic circuitry can be configured to wirelessly communicate with the controller. The at least one wound dressing can include a plurality of wound dressings. Each wound dressing of the plurality of wound dressings can include the electronic circuitry. The controller can be configured to at least one of: automatically adjust one or more operational parameters of the negative pressure wound therapy device based on one or more time durations during which the plurality of wound dressings have been in used or generate an indication responsive to a determination that therapy settings associated with at least some wound dressings of the plurality of wound dressings are incompatible.

A method of operating a negative pressure wound therapy system can include, by electronic circuitry of at least one wound dressing configured to be positioned over a wound and connected to a negative pressure source configured to provide negative pressure to the wound, monitoring a time duration during which the at least one wound dressing has been in use and communicating dressing usage information to a controller of a negative pressure wound therapy device. The method can include, by the controller of the negative pressure wound therapy device, automatically adjusting one or more operational parameters of a negative pressure wound therapy device based the dressing usage information.

The method of any of the preceding paragraphs and/or any of the methods disclosed herein can include one or more of the following features. The method can include, by the controller, responsive to an indication from the electronic circuitry that the time duration during which the at least one wound dressing has been in use satisfies an operational lifetime of the at least one wound dressing, performing at least one of: disabling operation of the negative pressure source or providing a dressing change indication. The electronic circuitry can be configured to monitor pressure proximal to the wound. The method can include, by the electronic circuitry, initiating monitoring of the time duration during which the at least one wound dressing has been in use responsive to determining at least one of: initial activation of the negative pressure source or initial attainment of a threshold negative pressure level proximal to the wound. The method can include, by the electronic circuitry, pausing monitoring the time duration during which the at least one wound dressing has been in use responsive to receiving an indication from the controller that provision of negative pressure by the negative pressure source has been interrupted. The method can include, by the electronic circuitry, resuming monitoring the time duration during which the at least one wound dressing has been in use responsive to receiving an indication from the controller that provision of negative pressure by the negative pressure source has been resumed.

The method of any of the preceding paragraphs and/or any of the methods disclosed herein can include one or more of the following features. The method can include, by the electronic circuitry, providing an indication of the time duration during which the at least one wound dressing has been in use responsive to determining that the time duration during which the at least one wound dressing has been in use satisfies a duration threshold, the duration threshold being shorter than an operational lifetime of the at least one wound dressing. The at least one wound dressing can include a plurality of wound dressings. Each wound dressing of the plurality of wound dressings can include the electronic circuitry. The method can include, by the controller, performing at least one of: automatically adjusting one or more operational parameters of the negative pressure wound therapy device based on one or more time durations during which the plurality of wound dressings have been in used or generating an indication responsive to determining that therapy settings associated with at least some wound dressings of the plurality of wound dressings are incompatible.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Embodiments of the present disclosure will now be described hereinafter, by way of example only, with reference to the accompanying drawings in which:

FIG. 1 illustrates a negative pressure wound therapy system.

DETAILED DESCRIPTION

Figure 2A:
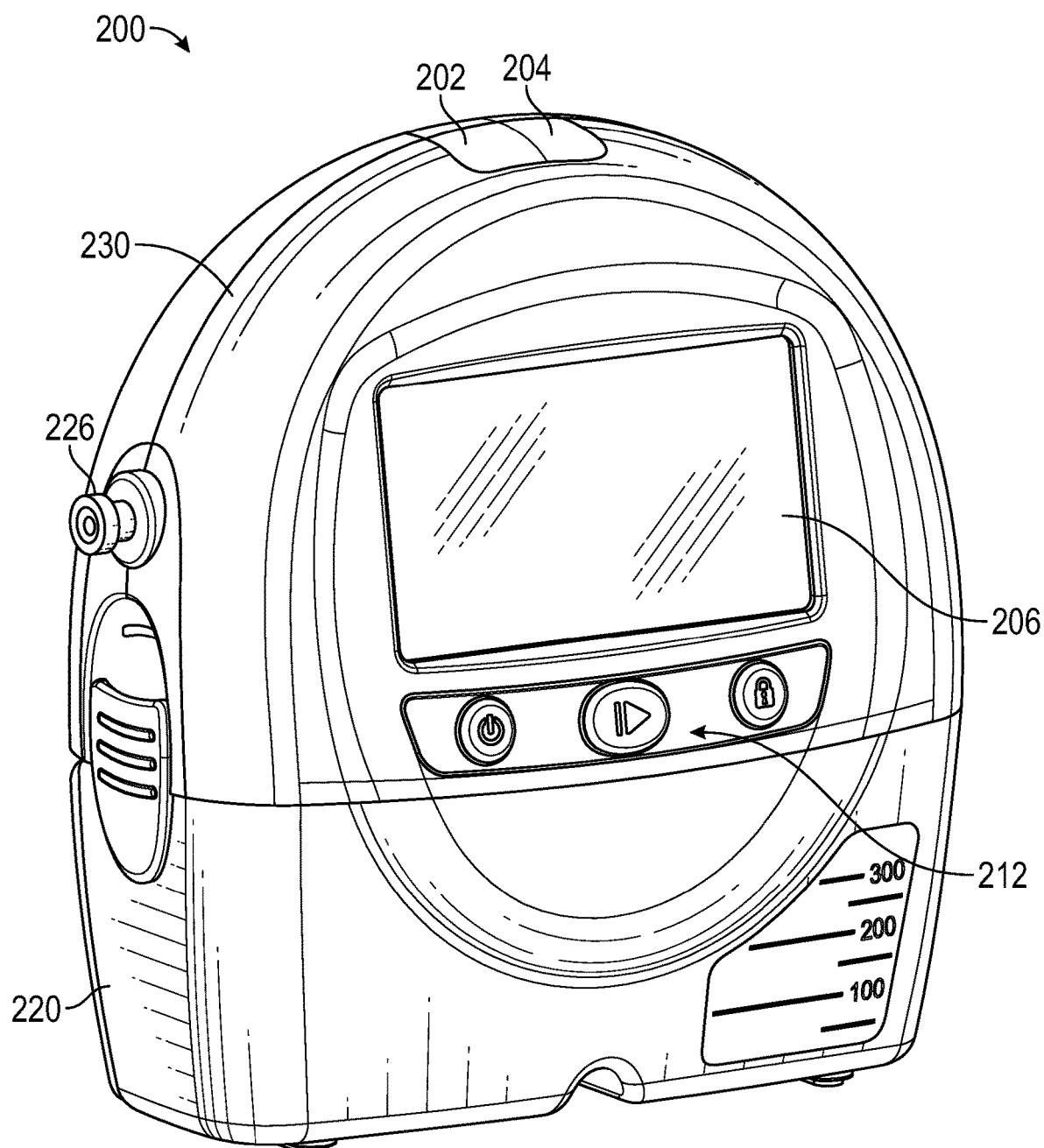
FIGS. 2A and 2B illustrate a negative pressure wound therapy device and canister.

Throughout this specification reference is made to a wound. The term wound is to be broadly construed and encompasses open and closed wounds in which skin is torn, cut or punctured or where trauma causes a contusion, or any other superficial or other conditions or imperfections on the skin of a patient or otherwise that benefit from pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Embodiments or arrangements disclosed herein relate to methods and apparatuses for dressing and treating a wound with topical negative pressure (TNP) therapy. For example, but without limitation, any embodiments disclosed herein may relate to treating a wound with reduced pressure (sometimes referred to as negative pressure) provided from a pump kit. Although not required, any embodiments of the pump kit can be sterile. As another non-limiting example, any embodiments disclosed herein relate to apparatuses and methods for controlling the operation of a TNP system. In some aspects, this disclosure generally relates to systems, methods, and devices for activating or controlling a medical device, in particular, for activating or controlling a pump assembly of a negative pressure wound therapy system.

Some aspects of the present disclosure relate to systems and methods of treating a wound with reduced pressure. Some aspects of the present disclosure are generally applicable to use in topical negative pressure (TNP) or reduced pressure therapy systems. Briefly, negative pressure wound therapy (NPWT) assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability. As used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects pressure that is X mmHg below 760 mmHg or, in other words, a pressure of (760−X) mmHg. In addition, negative pressure that is "less" or "smaller" than X mmHg corresponds to pressure that is closer to atmospheric pressure (for example, −40 mmHg is less than −60 mmHg). Negative pressure that is "more" or "greater" than −X mmHg corresponds to pressure that is further from atmospheric pressure (for example, −80 mmHg is more than −60 mmHg). In some cases, local ambient atmospheric pressure is used as a reference point, and such local atmospheric pressure may not necessarily be, for example, 760 mmHg.

Systems and methods disclosed herein can be used with other types of treatment in addition to or instead of reduced pressure therapy, such as irrigation, ultrasound, heat or cold, neuro stimulation, or the like. In some cases, disclosed systems and methods can be used for wound monitoring without application of additional therapy. Systems and methods disclosed herein can be used in conjunction with a dressing, including with compression dressing, reduced pressure dressing, or the like.

Overview

A health care professional (HCP) can be presented with a bewildering array of dressings that can be used on wounds. Different dressing-types can be better suited for different types of wounds and may require different operational parameters of the pump assembly that applies negative pressure to the wound. Correctly matching the operational parameters of the pump assembly to the type of dressing that is attached to the pump can allow optimal dressing performance and promote effective negative pressure wound therapy. Unless the HCP is a wound care expert, setting up the NPWT pump for optimal performance can involve some guesswork, or the pump may simply be left at the default settings. This is especially so if the operator is the patient, who will likely not have had any wound care education.

In NPWT-patient settings, and in other patient-care settings as well, activation of an electrical medical device and prescription of a therapy regime delivered by the device can be complex for a user to set or program into the device. The device can have a user interface with multiple options and indications for the user to select. For example, a pump assembly of a NPWT system can allow a user to select multiple therapy options such as the wound pressure, the temporal variation of wound pressure intensity, the volume of fluid infused into the wound, the pressure of the fluid infused into the wound, the time of therapy, and other operational parameters of the pump assembly. Medical devices other than NPWT pump assemblies also have operational parameters that are complex for a user to set or program into the device. For the sake of clarity, the systems and methods of the present disclosure are described herein often in terms of NPWT systems. However, the present disclosure is not limited to NPWT medical devices and can be applied to the activation and operation of medical devices in general.

The NPWT systems of the present disclosure can link the dressing and the pump assembly such that the pump assembly is automatically informed of the optimal operational parameters to apply to the dressing. The dressing can automatically inform a controller of the pump assembly one or more pieces of information about the identity of the dressing that is attached to the pump assembly. The dressing can include a sensor (e.g., pressure sensor) that wirelessly transmits data (e.g., dressing information) to a controller in the pump assembly. The controller can modify the operational parameters of the pump assembly based on the dressing information received from the dressing such that the pump assembly applies the appropriate operational parameters to the dressing. Such linking of the dressing to the pump assembly can be performed automatically (for example, at initialization of therapy) and facilitate more optimal treatment of the wound.

Wound Therapy System

FIG. 1 illustrates a negative pressure wound treatment system 100 (sometimes referred to as a reduced pressure wound therapy system, a TNP system, or a wound treatment system) comprising a wound filler 130 placed inside a wound cavity 110, the wound cavity 110 sealed by a wound cover 120. The wound filler 130 in combination with the wound cover 120 can be referred to as a wound dressing. A conduit 140 (such as a single or multi lumen tube) is connected the wound cover 120 with a wound therapy device 150 (sometimes as a whole or partially referred to as a "pump assembly") configured to supply reduced or negative pressure. The wound cover 120 can be in fluidic communication with the wound cavity 110.

With any of the systems disclosed herein, a wound therapy device can be canisterless (meaning that exudate is collected in the wound dressing or is transferred via the conduit 140 for collection to another location). However, any of the wound therapy devices disclosed herein can include or support a canister.

Additionally, with any of the wound therapy systems disclosed herein, any of the wound therapy devices can be mounted to or supported by the wound dressing, or adjacent to the wound dressing. The wound filler 130 can be any suitable type, such as hydrophilic or hydrophobic foam, gauze, inflatable bag, and so on. The wound filler 130 can be conformable to the wound cavity 110 such that it substantially fills the wound cavity 110. The wound cover 120 can provide a substantially fluid impermeable seal over the wound cavity 110. In some cases, the wound cover 120 has a top side and a bottom side, and the bottom side adhesively (or in any other suitable manner) seals with the wound cavity 110. The conduit 140 or any other conduit disclosed herein can be formed from polyurethane, PVC, nylon, polyethylene, silicone, or any other suitable material.

The wound cover 120 can have a port (not shown) configured to receive an end of the conduit 140. In some cases, the conduit 140 can otherwise pass through or under the wound cover 120 to supply reduced pressure to the wound cavity 110 so as to maintain a desired level of reduced pressure in the wound cavity 110. The conduit 140 can be any suitable article configured to provide at least a substantially sealed fluid flow pathway or path between the wound therapy device 150 and the wound cover 120, so as to supply the reduced pressure provided by the wound therapy device 150 to wound cavity 110.

The wound cover 120 and the wound filler 130 can be provided as a single article or an integrated single unit. In some cases, no wound filler is provided and the wound cover by itself may be considered the wound dressing. The wound dressing may then be connected, via the conduit 140, to a source of negative pressure of the wound therapy device 150. In some cases, though not required, the wound therapy device 150 can be miniaturized and portable, although larger conventional negative pressure sources (or pumps) can also be used.

The wound cover 120 can be located over a wound site to be treated. The wound cover 120 can form a substantially sealed cavity or enclosure over the wound site. The wound cover 120 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate. The wound therapy system can operate with or without the use of an exudate canister.

The wound therapy system can support an exudate canister. In some cases, configuring the wound therapy device 150 and conduit 140 so that the conduit 140 can be quickly and easily removed from the wound therapy device 150 can facilitate or improve the process of wound dressing or pump changes, if necessary. Any of the pump assemblies disclosed herein can have any suitable connection between the conduit 140 and the pump.

The wound therapy device 150 can deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some cases, the pressure range can be between about −40 mmHg and −150 mmHg. Alternatively, a pressure range of up to −75 mmHg, up to −80 mmHg or over −80 mmHg can be used. Also in some cases a pressure range of below −75 mmHg can be used. Alternatively, a pressure range of over approximately −100 mmHg, or even −150 mmHg, can be supplied by the wound therapy device 150.

The wound therapy device 150 can provide continuous or intermittent negative pressure therapy. Continuous therapy can be delivered at above 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points (sometimes referred to as setpoint). Low set point can be set at above 0 mmHg, −25 mmHg, −40 mmHg, −50 mmHg, d-60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values.

In operation, the wound filler 130 can be inserted into the wound cavity 110, and wound cover 120 can be placed so as to seal the wound cavity 110. The wound therapy device 150 can provide negative pressure to the wound cover 120, which may be transmitted to the wound cavity 110 via the wound filler 130. Fluid (such as, wound exudate) can be drawn through the conduit 140 and stored in a canister. In some cases, fluid is absorbed by the wound filler 130 or one or more absorbent layers (not shown).

Wound dressings that may be utilized with the pump assembly and systems of the present application include Renasys-F, Renasys-G, Renasys AB, and Pico Dressings available from Smith & Nephew. Further description of such wound dressings and other components of a negative pressure wound therapy system that may be used with the pump assembly and systems of the present application are found in U.S. Patent Publication Nos. 2012/0116334, 2011/0213287, 2011/0282309, 2012/0136325 and U.S. Pat. No. 9,084,845, each of which is incorporated by reference in its entirety. In some cases, other suitable wound dressings can be utilized.

Figure 2B:
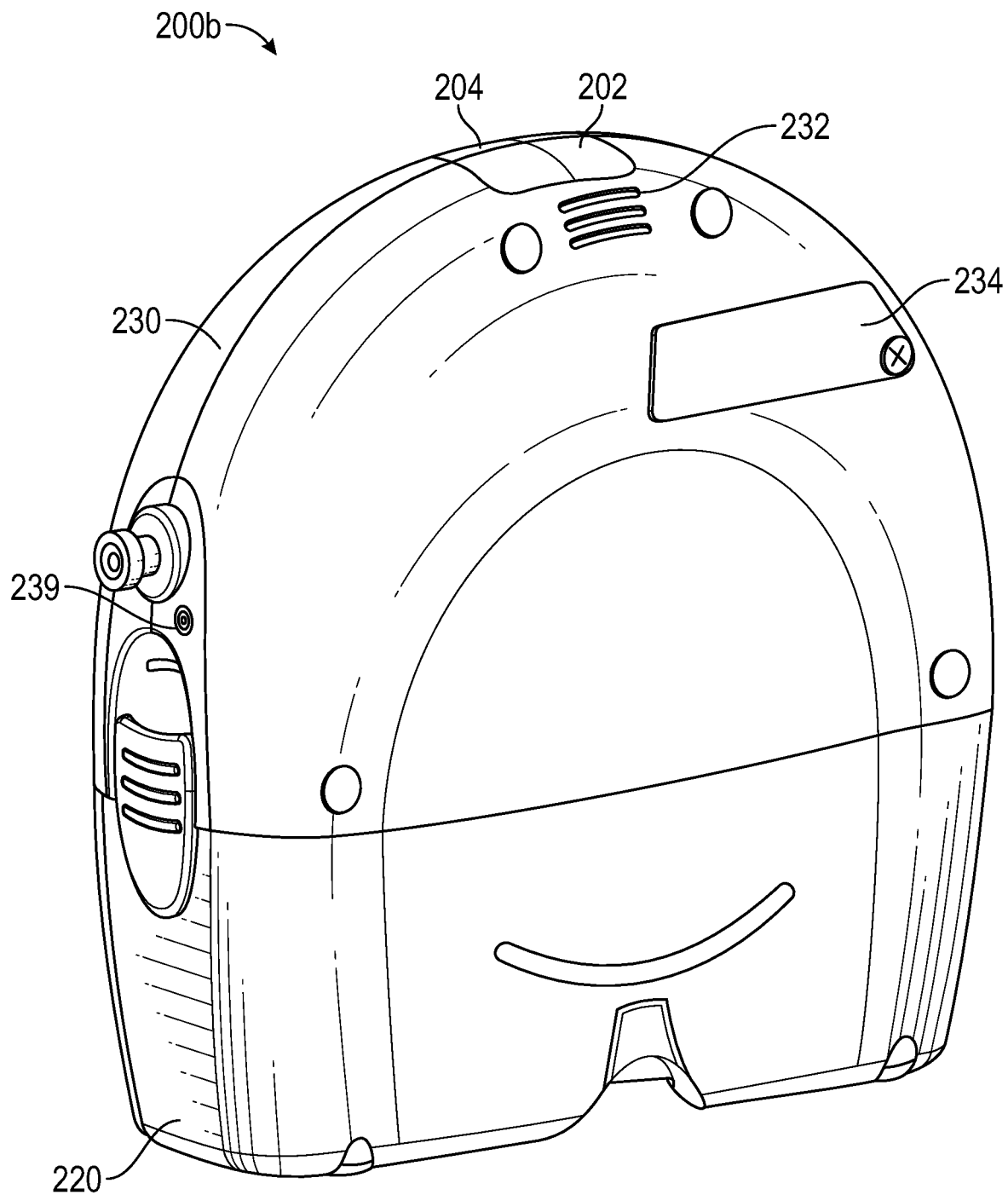

FIGS. 2A and 2B illustrates a negative pressure wound therapy device 200 (sometimes referred to as a wound therapy device) including a pump assembly 230 and a canister 220. As illustrated, the pump assembly 230 and the canister 220 can be connected, thereby forming the wound therapy device 200. The pump assembly 230 can include one or more indicators, such as visual indicator 202 configured to indicate alarms and visual indicator 204 configured to indicate status of the pump assembly 230. The visual indicators 202 and 204 can alert a user (for example, patient, health care provider, or the like) to a variety of operating or failure conditions of the pump assembly 230, including alerting the user to normal or proper operating conditions, pump failure, power supplied to the pump or power failure, detection of a leak within the wound cover or flow pathway (sometimes referred to as fluid flow path), suction blockage in the flow pathway, canister full, overpressure, or any other similar or suitable conditions or combinations thereof. Any one or more suitable indicators can be additionally or alternatively used, such as visual, audio, tactile indicator, and so on. The pump assembly 230 can include a display 206 (such as a screen) mounted in a recess formed in a case of the pump assembly 230. The display 206 can be a touch screen display. The display 206 can support playback of audiovisual (AV) content, such as instructional videos, and render a number of screens or graphical user interfaces (GUIs) for configuring, controlling, and monitoring the operation of the pump assembly 230. The pump assembly 230 can include one or more strap mounts 226 for connecting a carry strap to the pump assembly 230 or for attaching a cradle. The canister 220 may be replaced with another canister, such as when the canister 220 has been filled with fluid.

The pump assembly 230 can include buttons 212 (such as keys) that allow the user to operate and monitor the operation of the pump assembly 230. One of the buttons 212 can operate as a power button to turn on/off the pump assembly 230. Another of the buttons 212 can operate as a play/pause button for the delivery of therapy.

The canister 220 can hold fluid (such as, exudate) removed from the wound cavity 110. The canister 220 includes one or more latches for attaching the canister to the pump assembly 230. For example, the canister 220 as illustrated can have a capacity of 300 mL and include graduations. The canister 220 can include a tubing channel for connecting to the conduit 140. FIG. 2B illustrates a rear view 200B of the pump assembly 230 and the canister 220.

The pump assembly 230 can include a speaker 232 for producing sound. The speaker 232 can generate an acoustic alarm in response to deviations in therapy delivery, non-compliance with therapy delivery, or any other similar or suitable conditions or combinations thereof.

The pump assembly 230 can include a filter access door 234 for accessing and replacing one or more filters, such as antibacterial filters. The pump assembly 230 can comprise a power jack 239 for charging and recharging an internal battery of the pump assembly. The pump assembly 230 can include a disposable power source, such as batteries, so that no power jack is needed.

Figure 3:
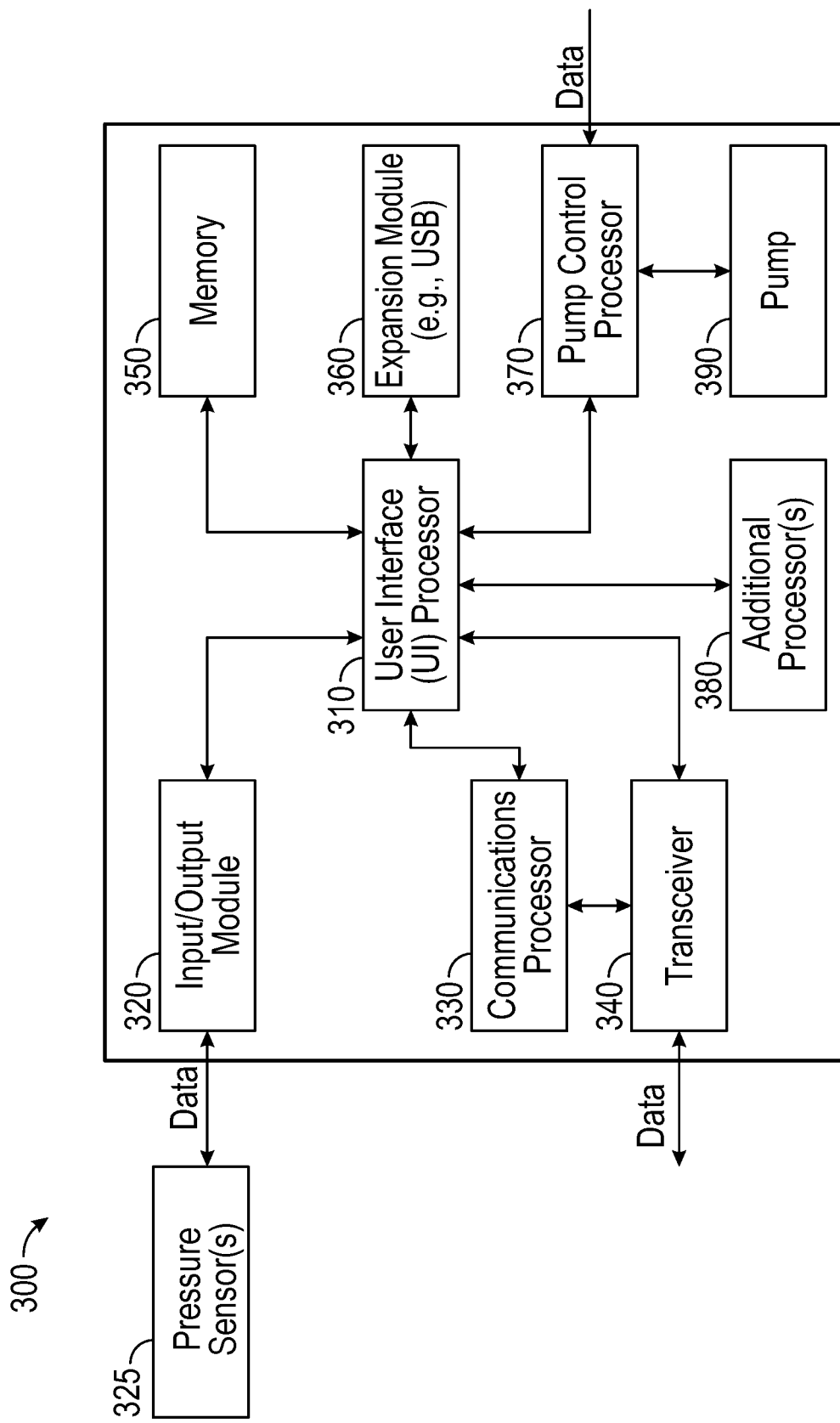
FIG. 3 illustrates a schematic of a negative pressure wound therapy device.

FIG. 3 illustrates a schematic of a control system 300 which can be employed in the wound monitoring or treatment systems described herein, such as in the wound therapy device 200 of FIGS. 2A and 2B. Electrical components can operate to accept user input, provide output to the user, operate the pressure source, provide network connectivity, and so on. A first processor can be responsible for user activity, and a second processor can be responsible for controlling another device, such as a pump 390. Input and output to the other device, such as a pump 390, one or more sensors (for example, one or more pressure sensors 325 configured to monitor pressure in one or more locations of the fluid flow path), or the like, can be controlled by an input/output (I/O) module 320. For example, the I/O module can receive data from one or more sensors through one or more ports, such as serial (for example, I2C), parallel, hybrid ports, and the like. The processor 310 can receive data from and provide data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, can store data in memory 350 (such as one or more memory modules), which can be internal or external to the processor 310. Any suitable type of memory can be used, including volatile or non-volatile memory, such as RAM, ROM, magnetic memory, solid-state memory, Magnetoresistive random-access memory (MRAM), and the like.

The processor 310 can be a general purpose controller, such as a low-power processor, or an application specific processor. The processor 310 can be configured as a "central" processor in the electronic architecture of the control system 300, and the processor 310 can coordinate the activity of other processors, such as a pump control processor 370, communications processor 330, and one or more additional processors 380. The processor 310 can run a suitable operating system, such as a Linux, Windows CE, VxWorks, etc.

The pump control processor 370 can control the operation of a pump 390, which can generate negative or reduced pressure. The pump 390 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. The pump control processor 370 can measure pressure in a fluid flow path, using data received from one or more pressure sensors 325, calculate the rate of fluid flow, and control the pump. The pump control processor 370 can control the pump motor so that a desired level of negative pressure is achieved in the wound cavity 110. The desired level of negative pressure can be pressure set or selected by the user. The pump control processor 370 can control the pump (for example, pump motor) using pulse-width modulation (PWM). A control signal for driving the pump can be a 0–100 % duty cycle PWM signal. The pump control processor 370 can perform flow rate calculations and detect alarms. The pump control processor 370 can communicate information to the processor 310. The pump control processor 370 can be a low-power processor.

A communications processor 330 can provide wired or wireless connectivity. The communications processor 330 can utilize one or more transceivers 340 for sending and receiving data. The one or more transceivers 340 can include one or more antennas, optical sensors, optical transmitters, vibration motors or transducers, vibration sensors, acoustic sensors, ultrasound sensors, or the like. The communications processor 330 can provide one or more of the following types of connections: Global Positioning System (GPS), cellular connectivity (for example, 2G, 3G, LTE, 4G, 5G, or the like), near field communication (NFC), Bluetooth connectivity, radio frequency identification (RFID), wireless local area network (WLAN), wireless personal area network (WPAN), WiFi connectivity, Internet connectivity, optical connectivity (for example, using infrared light, barcodes, such as QR codes, etc.), acoustic connectivity, ultrasound connectivity, or the like. Connectivity can be used for various activities, such as pump assembly location tracking, asset tracking, compliance monitoring, remote selection, uploading of logs, alarms, and other operational data, and adjustment of therapy settings, upgrading of software or firmware, pairing, and the like.

The communications processor 330 can provide dual GPS/cellular functionality. Cellular functionality can, for example, be 3G, 4G, or 5G functionality. The communications processor 330 can communicate information to the processor 310. The communications processor 330 can include internal memory or can utilize memory 350. The communications processor 330 can be a low-power processor.

The control system 300 can store data, such as GPS data, therapy data, device data, and event data. This data can be stored, for example, in memory 350. This data can include patient data collected by one or more sensors. The control system 300 can track and log therapy and other operational data. Such data can be stored, for example, in the memory 350.

Using the connectivity provided by the communications processor 330, the control system 300 can upload any of the data stored, maintained, or tracked by the control system 300 to a remote computing device. The control system 300 can also download various operational data, such as therapy selection and parameters, firmware and software patches and upgrades, and the like. The one or more additional processors 380, such as processor for controlling one or more user interfaces (such as, one or more displays), can be utilized. In some cases, any of the illustrated or described components of the control system 300 can be omitted depending on an embodiment of a wound monitoring or treatment system in which the control system 300 is used.

Any of the negative pressure wound therapy devices described herein can include one or more features disclosed in U.S. Pat. No. 9,737,649 or U.S. Patent Publication No. 2017/0216501, each of which is incorporated by reference in its entirety.

Dressing Recognition and Therapy Adjustment

Figure 4:
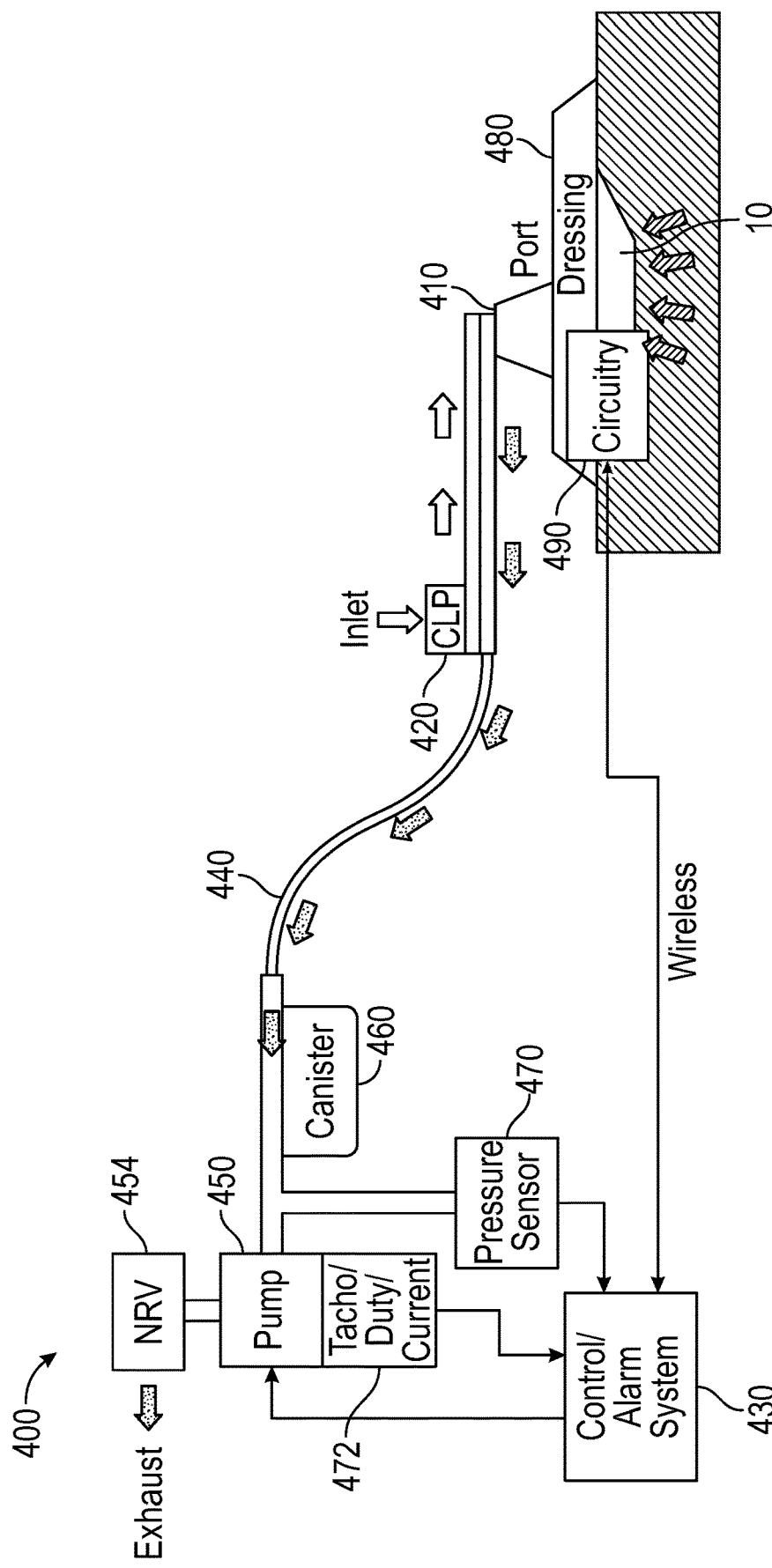
FIG. 4 illustrates a reduced pressure wound therapy system including a pump assembly.

FIG. 4 illustrates a NPWT system 400, which can include one or more components of any of the systems disclosed herein. For example, the system 400 can include one or more components of the device 200. The system 400 can include one or more of: a fluidic connector 410, which can be a soft port (such as a Renasys Soft Port available from Smith & Nephew or a fluidic connector as described in U.S. Pat. No. 8,801,685, the entirety of which is hereby incorporated by reference), a controlled leak path (CLP) 420 provided at a proximal end or inlet (and/or another portion) of the fluidic connector 410, a controller 430 (which can be similar to one more elements of the control system 300), a conduit 440 connected to a proximal end of the fluidic connector 410, a negative pressure source 450, a pressure sensor 470 (which can be configured to measure pressure in an inlet of the negative pressure source 450), a wound dressing 480, and electronic circuitry 490. The electronic circuitry 490 can include one or more of: a controller, a sensor (for example, dressing (or wound) pressure sensor configured to measure pressure at the wound), communication electronics configured to one or more transmit to or receive data from the controller 430. Communication electronics can include a transceiver, as disclosed herein. For instance, communication electronics can be configured to communicate wirelessly, such as using Bluetooth, Zigbee, or the like. As another example, communication electronics can be configured to communicate over a wired connection or over a connection that is both wired and wireless. The electronic circuitry 490 can be at least partially supported by (such as, embedded into) the wound dressing 480 and/or the fluidic connector 410 (as illustrated, for example, in FIG. 5).

In some cases, as described herein, the canister 460 may not be present. The dressing 480 can be sealed over the wound 10. The conduit 440 can fluidically connect the negative pressure source 450 to the wound space (or volume) enclosed by the dressing 480. One or more of the negative pressure source 450, canister 460, conduit 440, CLP 420, fluidic connector 410, or dressing 480 can form a fluid flow path via which the negative pressure source 450 can aspirate fluid from the wound 10. The negative pressure source 450 can apply negative pressure to the wound 10 through the conduit 440. As illustrated, the system 400 can include the exhaust 454 configured to expel gas aspirated by the negative pressure source 450. The exhaust can include a one-way valve, such as a non-return valve, configured to permit fluid flow (for example, gas flow) in one direction. The controller 430 can control operation of the negative pressure source. As disclosed herein (for instance, in connection with FIGS. 2A-2B), one or more of the negative pressure source 450, exhaust 454, load sensor 472, pressure sensor 470, and controller 430 can be supported by (such as, enclosed within) a housing, thereby forming a device or pump assembly.

The CLP 420 can provide a controlled flow of gas (such as, atmospheric air) to the wound 10 from the inlet of the fluid connector to the dressing. The load sensor 472 (e.g., tachometer) can monitor and inform the controller 430 of the performance (e.g., operating speed) of the negative pressure source 450. The load sensor 472 can monitor activity of the negative pressure source 450. The CLP 420 can be used in conjunction with the conduit pressure sensor 470 and the load sensor 472 to evaluate whether there is a blockage in the conduit 140 (and/or fluid flow path) or a leakage in the fluid flow path (such as, in the seal between the dressing 480 and the wound 10). For example, the load sensor 472 can be a tachometer that informs the controller 430 of the operating speed of the negative pressure source 450.

The controller 430 can receive one or more pressure readings from the conduit pressure sensor 470 and evaluate whether the expected negative pressure supplied by the negative pressure source 450 operating at the speed indicated by the tachometer matches the one or more pressure readings from the conduit pressure sensor 470. In some arrangements, the CLP 420, the pressure in the conduit 440 (as measured by the conduit pressure sensor 470), and the operating performance on the negative pressure source 450 (as measured by the load sensor 472) can be interpreted by the controller 430 to evaluate whether to signal an alarm. The system can signal a leak alarm. The system can signal a blockage alarm. Any of the alarms or indications described herein can include one or more of visual, audible, tactile, or the like indications. For instance, the controller 430 can be in communication with one or more indicators configured to provide indication(s). In addition to or alternatively, any of the alarms or indications described herein can include transmission of information or data to a remote computing device.

The NPWT system 400 can have a wound pressure sensor and not a conduit pressure sensor 470 (or vice versa). The electronic circuitry can wirelessly (or via a wired connection) communicate to the controller 430 wound pressure measured by the wound pressure sensor. The wound pressure sensor can be located within the wound space that is enclosed by the wound dressing 480. For example, the wound pressure sensor can be at least partially supported by the dressing 480. In such arrangements, the wound pressure sensor can have the advantage of detecting the wound pressure directly. The wound pressure sensor can detect blockages in the fluid flow path (such as, at or in the fluidic connector 410) more easily and reliably than can the conduit pressure sensor 470. For example, the controller 430 can evaluate whether the wound pressure (as detected by the wound pressure sensor) matches the expected wound pressure corresponding to the operating performance of the negative pressure source 450 (as detected from the load sensor 472), as discussed herein. In some cases, the wound pressure sensor can be positioned in the port 410, as illustrated by 590A and 590B in FIG. 5.

One or more wound pressure sensors can allow the system 400 to more reliably treat two or more wounds. For example, two conduits 440 connected to two separate dressings can each be connected to the negative pressure source 450 through a Y-junction or Y-connector (see, for example, 555 in FIG. 5). Each of the two conduits 440 can deliver negative pressure from the negative pressure source 450 to a wound space enclosed by a dressing 480. A conduit pressure sensor 470 measuring pressure at the trunk of the Y-junction cannot determine as easily or reliably which, if any, of the two conduits 440 is blocked or which, if any, of the two wound dressings 480 is leaking. By contrast, a wound pressure sensor disposed in each of the two dressings 480 can independently evaluate the wound pressure at the corresponding wound 10. As will be appreciated, a wound pressure sensor located in the wound 10 can avoid hydrostatic issues of the conduit 440, making the system 400 more accurate and reliable for wounds at different heights and hydrostatic pressure heads. The wound pressure sensor can also avoid having to measure the wound pressure through an intervening canister 460, as is the case of the conduit pressure sensor 470 disposed between the canister 460 and the negative pressure source 450.

In addition to transmitting pressure information to the controller 430, the electronic circuitry 490 can wirelessly transmit dressing information to the controller 430 to inform the controller 430 about properties of one or more of the dressing 480 that is connected to the negative pressure source 450 or the wound 10. The wound pressure sensor can be positioned at different locations within the dressing 480. The wound pressure sensor can be disposed at any of the layers of the dressing 480 such as, for example, a wound contact layer, a wound filler layer, a foam layer, an absorbent layer, and a film layer. The wound pressure sensor can monitor one or more of dressing or wound operational information such as temperature, which can be useful for monitoring therapy, especially if the wound pressure sensor is located close to the wound 10 (e.g., at the wound contact layer). The electronic circuitry 490 can include a memory storing the dressing information. The memory can be read-only memory.

The dressing information transmitted to the controller 430 by the electronic circuitry 490 can be an identifier that informs the controller 430 of the dressing type being used. Such identifier can be unique to each electronic circuitry 490. The identifier could include parameterized information such as mode of operation (e.g., canister-mode or canisterless-mode), dressing size (e.g., area, capacity, or the like), controlled leak rate (e.g., CLP operational parameters), wound contact layer material (e.g., silicone), etc. The transmitted dressing information can provide functional information, such as the optimum negative pressure to apply to the wound 10 and whether to apply negative pressure to the wound 10 in a continuous or discontinuous fashion. Wound dressing 480 can be configured to be used for a limited duration of time (sometimes referred to as operational lifetime). At the end of the operational lifetime, the wound dressing 480 may need to be replaced. For example, Pico dressing sold by Smith & Nephew can be configured to be worn for 7 days. As another example, Renasys-F foam dressing available from Smith & Nephew can be configured to be worn for 3 days. As yet another example, Renasys-G gauze dressing available from Smith & Nephew can be configured to be worn for 5 days. As yet further example, Acticoat 3 antimicrobial dressing available from Smith & Nephew can be configured to be worn for 3 days, and Acticoat 7 antimicrobial dressing available from Smith & Nephew can be configured to be worn for 7 days. For efficacy of therapy and patient safety, it may be undesirable to exceed the operational lifetime of the dressing. For example, Pico dressing may become saturated with exudate, foam of Renasys-F foam dressing may grow into the wound, or the like.

The dressing information can include operational lifetime of the dressing. Electronic circuitry 490 can monitor a duration of time during which the dressing is in use. For example, electronic circuitry 490 can implement a timer. In response to the duration of time satisfying (for example, reaching) the operational lifetime, indication can be communicated to the controller 430 to one or more of disable further provision of negative pressure with that dressing or provide an indication that that dressing needs to be replaced. The controller 430 can re-enable provision of negative pressure after the dressing has been replaced with a fresh dressing.

The controller 430 can determine that fresh dressing has been positioned over the wound based on unique dressing identifier transmitted by the electronic circuitry 490, as described herein. Additionally or alternatively, the controller 430 can determine that fresh dressing has been positioned over the wound based on the duration of time during which the dressing has been in use. For instance, if the duration of time communicated by the electronic circuitry 490 previously indicated that operational lifetime has been satisfied and presently the duration of time indicates that the dressing is at or near beginning of its use (such as, the duration being near or close to zero), the controller 430 can determine that dressing had been replaced. Additionally or alternatively, a user can indicate that dressing has been replaced, such through the user interface.

Electronic circuitry 490 can initiate monitoring the duration of time in response to activation of the negative pressure source 450, which can cause a pressure decrease to be sensed by the wound pressure sensor. For example, initial activation of the negative pressure source 450 can cause a pressure decrease that satisfies a pressure decrease threshold associated with initiating monitoring of the duration of time. As another example, electronic circuitry 490 can initiate monitoring of the duration of time in response to initial attainment of a negative pressure set point at the wound as sensed by the wound pressure sensor. Negative pressure set point can be included in the dressing information. Electronic circuitry 490 can continue monitoring the duration of time following the initiation of monitoring irrespective of any interruptions in the provision of NPWT.

In some cases, electronic circuitry 490 can pause monitoring the duration of time in response to interruption in the provision of therapy (or NPWT). Such pause can correspond to the time of therapy interruption. The controller 430 can indicate to the electronic circuitry 490 that therapy has been interrupted (and/or restarted). Alternatively or additionally, electronic circuitry 490 can determine that therapy has been interrupted responsive to determining a pressure increase (such as, a pressure increase or total pressure that satisfies a pressure increase threshold). Alternatively or additionally, the controller 430 can monitor the duration of time and determine whether it satisfies the operational lifetime.

An indication of the duration of time (or remaining period of time for wearing the dressing) can be provided by one or more of the electronic circuitry 490 or controller 430. For example, indication can be provided before the operational lifetime has been reached (such as, 1 day before or the like). This could alert the user to an impending dressing change.

Alternatively or additionally, indication can be provided in response to reaching the operational lifetime. Indication can be provided using any of the approaches described herein, such as visually, audibly, and/or tactilely. The dressing 490 and/or the port 410 can include one or more indicators for providing the indication.

In situations when multiple wounds are being treated by the system, wound dressings for each of the wounds can include the electronic circuitry 490. Duration of time for each of the wound dressings can be monitored individually.

The packaging of the dressing 480 can give clear information on the types of wounds for which the dressing 480 is suitable (e.g., ulcer, trauma, high exudate, etc.), and this information can be automatically transmitted to the controller 430 upon connection of the dressing 480 to the negative pressure source 450. The information transmitted to the controller 430 by the electronic circuitry can be usage information (such as, operational lifetime of the dressing, how long the dressing 480 has been in use (or active), etc.), average pressure(s), or flow rate(s). Electronic circuitry 490 can monitor average pressure based on the readings of the wound pressure sensor. Averaging can facilitate removal of one or more errant pressure readings. Errant readings may be caused by flow of lumps of fluid, solids, or the like. A flow sensor (or flow meter) can be positioned in the fluid flow path. For instance, flow sensor can be positioned in the port 410. Electronic circuitry 490 can transmit flow information monitored by the flow sensor, for example, to the controller 430. In some cases, flow information monitored by the flow sensor can be filtered (such as, averaged) to remove errant flow readings. Flow information can be utilized to determine presence of leak (associated with high flow), blockage (associated with low flow), or the like. Flow information can be advantageously utilized to determine state of one of the wounds in a system treating a plurality of wounds, as described herein. For instance, a higher flow rate may be associated with more exudate being aspirated, which can be indicative of infection.

In some cases, when the electronic circuitry 490 first pairs to the device (such as, to the controller 430), the electronic circuitry 490 sends out the dressing identifier. Pairing can be performed via a communication protocol, such as Bluetooth, Zigbee, or the like. The device (such as, the controller 430) can use the dressing identifier to set up the preferred therapy mode for the dressing 480. In some cases, the preferred therapy mode is a canisterless mode in which exudate is absorbed in the dressing. In some cases, the preferred therapy mode is a canister mode in which exudate is drawn into the canister 460.

In some cases, the dressing identifier can be used to disable or lockout operation of the negative pressure source 450. This can be performed, for example, if a canister 460 has been errantly connected to the NPWT system 400 and the dressing identifier indicates that the attached dressing 480 is intended for use in a canisterless mode of operation of the device. In some cases, the dressing identifier can be used to lockout operation of the negative pressure source 450 if the canister 460 has not been connected to the NPWT system 400 and the dressing identifier indicates that the attached dressing 480 is intended for use in a canister mode of operation of the device.

The NPWT system 400 can automatically enable the preferred wound negative pressure and the preferred continuous or discontinuous action mode to be automatically set into the device (such as, by the controller 430), thereby stopping any guesswork by the user. Additionally or alternatively, the alarms for the NPWT system 400 can be adjusted automatically. For example, a leak threshold for an alarm could be raised for a dressing 480 with an expected larger leak rate (such as, due to size of the dressing, the built in CLP, or the wound contact layer). A leak threshold for an alarm can be lowered for a dressing 480 having a smaller expected leak rate. The system 400 can also adjust pressure alarms based on the preferred pressure setting dictated or indicated by the dressing 480.

The dressing 480 or the packaging for the dressing 480 can include a code (e.g., bar code, pin code, QR code, or the like) that is provided to the device (such as, to the controller 430) to inform about the dressing 480 that is connected to the negative pressure source 450. In some cases, the code can be scanned by one or more sensors in communication with the controller 430 (such as, one or more optical sensors). In some cases, the transmission of the dressing identifier (for example, to the controller 430) can obviate the need for the user to enter a code or for the device to have additional components (e.g., keypad, scanner) that add complexity.

Multiple Wound Operation and Status Detection

Figure 5:
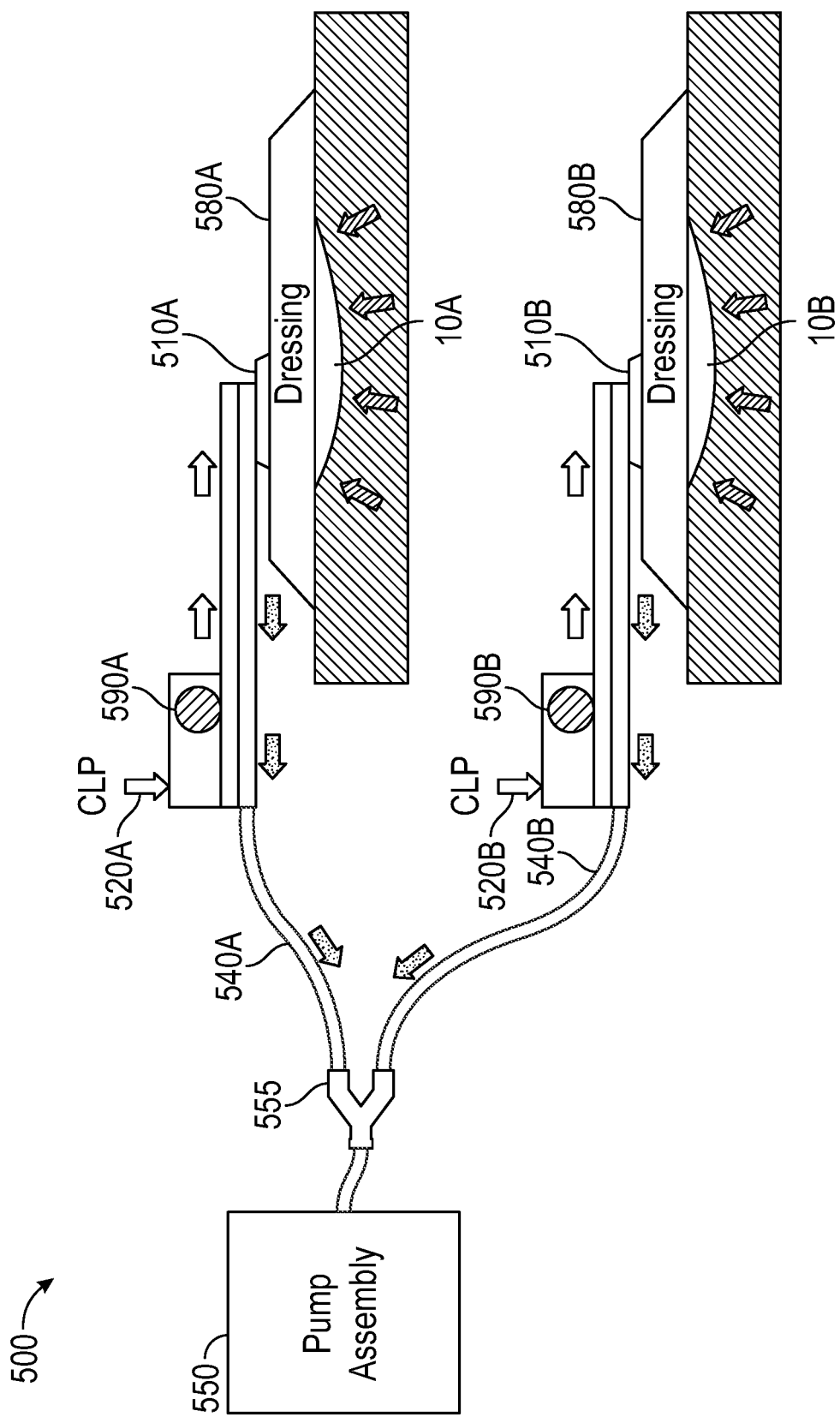
FIG. 5 illustrates a reduced pressure wound therapy system including a pump assembly fluidically connected to multiple wounds.

FIG. 5 illustrates a reduced pressure wound therapy system 500. Any of the components of the system 200 can function similarly to the respective components of the system 400. For example, a component labeled "5xx" (for example, "580A" or "580B") of the system 500 can function similarly to a respective component "4xx" (for example, "480") of the system 400. The system 500 can include a device or pump assembly 550 fluidically connected to a plurality of wounds 10A and 10B covered by wound dressings 580A and 580B. As described herein, the pump assembly 550 can be fluidically connected to the plurality of wounds via a plurality of conduits 540A and 540B. A Y-connector 555 can connect the pump assembly 550 to the plurality of conduits 540A and 540B. For example, a first branch of the Y-connector 555 can be connected to an inlet of the pump assembly 550 and a plurality of second branches of the Y-connector 555 can be connected to the plurality of conduits 540A and 540B. The pump assembly 550 can include one or more of a pressure sensor (such as, the pressure sensor 470), load sensor (such as, the load sensor 472), or controller (such as, the controller 430), as described herein. In some cases, a canister (such as, the canister 460) can also be provided.

A fluid flow path fluidically connecting the pump assembly 550 to any of the wounds can include a fluidic connector, such as 510A and 510B, as illustrated in FIG. 5 and described herein. Any of the connectors can be a Renasys Soft Port available from Smith & Nephew. Any of the fluidic connectors described herein can include or be made of non-rigid or substantially non-rigid material(s), such as the Renasys Soft Port connector. As described herein, controlled leak paths (CLP) 520A and 520B can be provided at a proximal end or inlet (and/or another portion) of any of the fluidic connectors, such as the connectors 510A or 510B. Any of the CLPs can admit gas (such as, atmospheric air) into a respective fluid flow path.

A plurality of electronic circuitries 590A and 590B are illustrated in FIG. 5. The electronic circuitries 590A and 590B can operate similarly to the electronic circuitry 490 described herein. As described herein, the electronic circuitries 590A and 590B can each include a pressure sensor positioned in a respective fluid flow path. For example, as illustrated in FIG. 5, a pressure sensor can be positioned in each of the fluid flow path. The pressure sensor(s) can monitor pressure in the fluid flow path(s). In some cases, the pressure sensor(s) can communicate monitored pressure(s) to the controller of the pump assembly 550. For example, one or more of the electronic circuitry(ies) can wirelessly or via a wired connection communicate measured pressure(s) to the controller of the system 500. The pressure sensors of the electronic circuities 590A and 590B can operate similarly to the pressure sensor of the electronic circuitry 490 described herein. For instance, the pressure sensors can measure pressure at or near the respective wound 10A and 10B. In some cases, any of the pressure sensors can be positioned on or in the respective fluidic connector, such as the connector 510A or 510B. For example, any of the pressure sensors can be positioned or embedded within a fluidic connector.

Pressure measured by any of the pressure sensors can be compared to a pressure threshold indicative of a minimum level of negative pressure for NPWT therapy. The pressure threshold can be about −60 mmHg or less or more, about −40 mmHg or less or more, about −25 mmHg or less or more, about −20 mmHg or less or more, or the like. In some cases, the pressure threshold can be dependent on a negative pressure setpoint of the negative pressure source. For example, the pressure threshold can be set at a fixed or variable offset relative to the negative pressure setpoint, such at about 10 mmHg or less or more, about 20 mmHg or less or more, about 25 mmHg or less or more, or the like. For instance, if the negative pressure setpoint is −80mmHg, the offset can be set at 20 mmHg, which results in the pressure threshold of −60 mmHg. The offset can be variable, such as proportionally decreasing as the negative pressure setpoint decreases. For example, a first offset associated with a first negative pressure setpoint can be smaller than a second offset associated with a second negative pressure setpoint that is larger (or more negative) than the first negative pressure setpoint.

In response to a determination that measured pressure satisfies the pressure threshold, it can be determined that there is loss of negative pressure in a particular fluid flow path (and/or wound) associated with the pressure sensor, which can be indicative of inadequate application of NPWT therapy to the particular wound. Loss of pressure can be due to one or more of blockages, leaks, or the like in the fluid flow path. Such determination of loss of pressure can be made by the controller of the system 500. For example, in response to a determination that pressure measured by the pressure sensor of the electronic circuitry 590A meets or falls below the pressure threshold, it can be determined that there is loss of negative pressure at the wound 10A, which can be indicative of inadequate application of NPWT therapy to the wound 10B.

Additionally or alternatively, in response to a determination that pressure measured by the pressure sensor of the electronic circuitry 590B meets or falls below the pressure threshold (or a different pressure threshold), it can be determined that there is loss of negative pressure at the wound 10B, which is indicative of inadequate application of NPWT therapy to the wound 10B. In some cases, any one or more of the pressure sensors can be paired with the controller. This can allow the controller to identify for which of the fluid flow paths (and/or wounds) pressure measurements are being provided. Pairing and/or monitoring of a wound can be performed, for example, via Bluetooth, Zigbee, or the like. In some cases, in addition to or instead of pairing, one or more pressure sensors can transmit an identifier configured to identify associated fluid flow path (and/or wound). For example, the identifier can be a dressing identifier as described herein. The identifier can be unique to each of the pressure sensors (or electronic circuitries).

Indication or alarm can be provided in response to a determination of loss or pressure in a particular fluid flow path (and/or wound). Indication can be provided by the controller. Indication can include any one or more of visual, audible, tactile, or the like indications or transmission of data to a remote computer. For instance, the pump assembly 550 can include one or more indicators that can be activated (for example, by the controller) to provide one or more indications. In some cases, indication can additionally or alternatively include modification of operation of the negative pressure source, such as increase in level of negative pressure provided by the negative pressure source, pausing operation of the negative pressure source, or the like. Provision of indication(s) can cause a user (such as, HCP) to perform one or more remedial actions with respect to provision of NPWT therapy, such as clearing a blockage (for example, by replacing a canister or dressing), fixing a leak in one or more fluid flow path(s), or the like.

In some cases, an indicator configured to provide any of the indications can be positioned in a fluid flow path. For example, an indicator can be positioned in each of the fluid flow paths, such as embedded in a fluidic connector and/or covered by a translucent material of the fluidic connector so that a visual indication can be provided to the user. Any of the indicators can communicate with the controller wirelessly or over a wired connection. The controller can activate and deactivate any of the indicators.

In some instances, any of the pressure sensors can include one or more indicators configured to provide any of the indications. For example, as described herein, any of the pressure sensors can be embedded within a fluidic connector. The pressure sensor can include a visual indicator covered by a translucent material of the fluidic connector so that a visual indication can be provided to the user. Any of the pressure sensors can detect loss of negative pressure and provide indication without involvement of the controller. Any of the pressure sensors can detect loss of negative pressure and provide an indication of the loss of negative pressure to the controller, which in turn can provide one or more indications to the user as described herein. For example, any of the pressure sensors can include a pressure switch configured to generate an indication in response to monitored pressure satisfying the pressure threshold. Additionally or alternatively, the controller can determine loss of negative pressure at one of the wounds and direct the associated pressure sensor to generate the indication.

Dressing identifiers associated with at least some wound dressing covering the wounds can indicate therapy settings that may be incompatible. For example, dressing identifier for a first wound dressing can indicate continuous provision of negative pressure by the negative pressure source, while dressing identifier for a second wound dressing can indicate intermittent provision of negative pressure by the negative pressure source. The controller can provide an indication in response to detecting incompatibility. The indication can be any of the indications disclosed herein. In some cases, the controller can be configured to resolve the incompatibility. In the above example, the controller could compromise between the two therapy settings by providing intermittent negative pressure using negative pressure set points and/or time intervals that are different than those associated with the second wound dressing.

Advantageously, the system 500 can determine loss of pressure indicative of insufficient application of NPWT therapy to a particular wound or wounds of a plurality of wounds. As described herein, remedial action can be taken by the user. This can prevent or limit interruptions of NPWT therapy as such interruptions can compromise the healing process, cause wound maceration, or the like.

Other Variations

Although certain embodiments described herein relate to wound dressings, systems and methods for use with negative pressure wound therapy, approaches disclosed herein are not limited to negative pressure wound therapy or medical applications. Systems and methods disclosed herein are generally applicable for use with other therapies, including ultrasound, instillation, or the like, and to medical or electronic devices in general, such as medical or electronic devices that can be worn by or applied to a user.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A negative pressure wound therapy system, comprising:
   first and second wound dressings configured to be positioned over a wound, the first and second wound dressings each comprising a respective electronic circuitry; and
   a negative pressure wound therapy device comprising:
      a negative pressure source configured to provide negative pressure to the wound via a fluid flow path connecting the negative pressure source to the first or second wound dressing; and
      a controller configured to operate the negative pressure source, wherein each of the electronic circuitries is configured to:
      communicate to the controller a dressing identifier, the dressing identifier indicating a negative pressure set point in the fluid flow path and an operational lifetime of the respective wound dressing, and
      monitor a time duration during which the respective wound dressing has been in use based on detecting an initial attainment of the negative pressure set point in the fluid flow path, and communicate to the controller the time duration, and
   wherein the controller is configured to:
      responsive to determining that a first time duration during which the first wound dressing has been in use received from the electronic circuitry of the first wound dressings satisfies the operational lifetime of the first wound dressing;
      disable operation of the negative pressure source and provide a wound dressing change indication, and
      resume operation of the negative pressure source responsive to determining that the first wound dressing has been replaced with the second wound dressing, wherein determining that the first wound dressing has been replaced with the second wound dressing is made responsive to detecting that a second time duration during which the second wound dressing has been in use communicated by the electronic circuitry of the second wound dressing indicates that the second wound dressing is at or near a beginning of being in use.

2. The negative pressure wound therapy system of claim 1, wherein each of the electronic circuitries comprises a pressure sensor configured to monitor pressure proximal to the wound.

3. The negative pressure wound therapy system of claim 2, wherein the initial attainment of the negative pressure set point in the fluid flow path is made based on one or more readings of the pressure sensor.

4. The negative pressure wound therapy system of claim 1, wherein the respective electronic circuitry is further configured to pause monitoring the respective time duration during which the first or second wound dressing has been in use responsive to receiving an indication from the controller that provision of negative pressure by the negative pressure source has been interrupted.

5. The negative pressure wound therapy system of claim 4, wherein the respective electronic circuitry is further configured to resume monitoring the respective time duration during which the first or second wound dressing has been in use responsive to receiving an indication from the controller that provision of negative pressure by the negative pressure source has been resumed.

6. The negative pressure wound therapy system of claim 1, wherein the respective electronic circuitry is further configured to provide an indication of the respective time duration during which the first or second wound dressing has been in use, the indication comprising of auditory, visual, or tactile indication.

7. The negative pressure wound therapy system of claim 6, wherein the respective electronic circuitry is configured to provide the indication responsive to a determination that the respective time duration during which the first or second wound dressing has been in use satisfies a duration threshold, the duration threshold being shorter than the operational lifetime of the first or second wound dressing.

8. The negative pressure wound therapy system of claim 7, wherein the indication is provided via at least one of the negative pressure wound therapy device or the first or second wound dressing.

9. The negative pressure wound therapy system of claim 1, wherein each of the electronic circuitries comprises memory configured to store the dressing identifier.

10. The negative pressure wound therapy system of claim 1, wherein the controller is further configured to automatically adjust an alarm threshold based on the dressing identifier.

11. The negative pressure wound therapy system of claim 10, wherein the controller is further configured to adjust a leak alarm threshold based on a leak rate of a controlled leak of the first or second wound dressing indicated by the dressing identifier.

12. The negative pressure wound therapy system of claim 1, wherein the dressing identifier is unique to each of the electronic circuitries.

13. The negative pressure wound therapy system of claim 1, wherein each of the electronic circuitries is configured to wirelessly communicate with the controller.

14. A method of operating a negative pressure wound therapy system, the method comprising:
by an electronic circuitry of a first wound dressing configured to be positioned over a wound and be connected by a fluid flow path to a negative pressure wound therapy device configured to provide a negative pressure to the wound:
communicating to the negative pressure wound therapy device a dressing identifier that comprises a negative pressure set point in the fluid flow path and an operational lifetime of the first wound dressing; and
monitoring a first time duration during which the first wound dressing has been in use based on detecting an initial attainment of the negative pressure set point in the fluid flow path, and
by the negative pressure wound therapy device:
responsive to determining that the first time duration during which the first wound dressing has been in use received from the electronic circuitry of the first wound dressing satisfies the operational lifetime of the first or second wound dressing:
disabling provision of the negative pressure and providing a wound dressing change indication, and
resuming operation of the negative pressure wound therapy device responsive to determining that the first wound dressing has been replaced with other a second wound dressing, wherein determining that the first wound dressing has been replaced with the second wound dressing is made responsive to detecting that a second time duration during which the second wound dressing has been in use communicated by an electronic circuitry of the second wound dressing indicates that the second wound dressing is at or near a beginning of being in use.

15. The method of claim 14, further comprising, by the respective electronic circuitry, pausing monitoring the respective time duration during which the first or second wound dressing has been in use responsive to receiving an indication from the negative pressure wound therapy device that provision of the negative pressure has been interrupted.

16. The method of claim 15, further comprising, by the respective electronic circuitry, resuming monitoring the respective time duration during which the first or second wound dressing has been in use responsive to receiving an indication from the negative pressure wound therapy device that provision of the negative pressure has been resumed.

17. The method of claim 14, further comprising, by the negative pressure wound therapy device, adjusting a leak alarm threshold based on a leak rate of a controlled leak of the first or second wound dressing indicated by the dressing identifier.

18. The method of claim 17, further comprising, by the respective electronic circuitry, providing an indication of the respective time duration during which the first or second wound dressing has been in use responsive to determining that the time duration during which the first or second wound dressing has been in use satisfies a duration threshold, the duration threshold being shorter than the operational lifetime of the first or second wound dressing.

19. The method of claim 14, wherein the dressing identifier is unique to each of the electronic circuitries.

* * * * *

UNITED STATES PATENT AND TRADEMARK OFFICE
CERTIFICATE OF CORRECTION

PATENT NO. : 12,161,533 B2
APPLICATION NO. : 17/977220
DATED : December 10, 2024
INVENTOR(S) : David Michael Elder et al.

It is certified that error appears in the above-identified patent and that said Letters Patent is hereby corrected as shown below:

In the Specification

In Column 7, Lines 1-34, delete
"Some aspects of the present disclosure relate to systems and methods of treating a wound with reduced pressure. Some aspects of the present disclosure are generally applicable to use in topical negative pressure (TNP) or reduced pressure therapy systems. Briefly, negative pressure wound therapy (NPWT) assists in the closure and healing of many forms of "hard to heal" wounds by reducing tissue edema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability. As used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects pressure that is X mmHg below 760 mmHg or, in other words, a pressure of (760–X) mmHg. In addition, negative pressure that is "less" or "smaller" than X mmHg corresponds to pressure that is closer to atmospheric pressure (for example, –40 mmHg is less than –60 mmHg). Negative pressure that is "more" or "greater" than –X mmHg corresponds to pressure that is further from atmospheric pressure (for example, –80 mmHg is more than –60 mmHg). In some cases, local ambient atmospheric pressure is used as a reference point, and such local atmospheric pressure may not necessarily be, for example, 760 mmHg." and insert --
Some aspects of the present disclosure relate to systems and methods of treating a wound
with reduced pressure. Some aspects of the present disclosure are generally applicable to use in
topical negative pressure (TNP) or reduced pressure therapy systems. Briefly, negative pressure
wound therapy (NPWT) assists in the closure and healing of many forms of "hard to heal" wounds by
reducing tissue edema, encouraging blood flow and granular tissue formation, or removing excess
exudate and can reduce bacterial load (and thus infection risk). In addition, the therapy allows for less
disturbance of a wound leading to more rapid healing. TNP therapy systems can also assist in the Signed and Sealed this
Eighteenth Day of February, 2025

Coke Morgan Stewart
*Acting Director of the United States Patent and Trademark Office*

CERTIFICATE OF CORRECTION (continued)
U.S. Pat. No. 12,161,533 B2 healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.
As used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects pressure that is X mmHg below 760 mmHg or, in other words, a pressure of (760–X) mmHg. In addition, negative pressure that is "less" or "smaller" than X mmHg corresponds to pressure that is closer to atmospheric pressure (for example, –40 mmHg is less than –60 mmHg). Negative pressure that is "more" or "greater" than –X mmHg corresponds to pressure that is further from atmospheric pressure (for example, –80 mmHg is more than –60 mmHg). In some cases, local ambient atmospheric pressure is used as a reference point, and such local atmospheric pressure may not necessarily be, for example, 760 mmHg.--.

In Column 9, Lines 18-36, delete
"The wound cover 120 can be located over a wound site to be treated. The wound cover 120 can form a substantially sealed cavity or enclosure over the wound site. The wound cover 120 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate. The wound therapy system can operate with or without the use of an exudate canister.
The wound therapy system can support an exudate canister. In some cases, configuring the wound therapy device 150 and conduit 140 so that the conduit 140 can be quickly and easily removed from the wound therapy device 150 can facilitate or improve the process of wound dressing or pump changes, if necessary. Any of the pump assemblies disclosed herein can have any suitable connection between the conduit 140 and the pump." and insert
--The wound cover 120 can be located over a wound site to be treated. The wound cover 120 can form a substantially sealed cavity or enclosure over the wound site. The wound cover 120 can have a film having a high water vapour permeability to enable the evaporation of surplus fluid, and can have a superabsorbing material contained therein to safely absorb wound exudate. In some cases, the components of the TNP systems described herein can be particularly suited for incisional wounds that exude a small amount of wound exudate.
The wound therapy system can operate with or without the use of an exudate canister. The wound therapy system can support an exudate canister. In some cases, configuring the wound therapy device 150 and conduit 140 so that the conduit 140 can be quickly and easily removed from the wound therapy device 150 can facilitate or improve the process of wound dressing or pump changes, if necessary. Any of the pump assemblies disclosed herein can have any suitable connection between the conduit 140 and the pump.--.

In Column 9, Line 58, delete "mmHg, d-60 mmHg," and insert --mmHg, -60 mmHg,--.

In Column 10, Lines 25-57, delete
"FIGS. 2A and 2B illustrates a negative pressure wound therapy device 200 (sometimes referred to as a wound therapy device) including a pump assembly 230 and a canister 220. As illustrated, the pump assembly 230 and the canister 220 can be connected, thereby forming the wound therapy device 200. The pump assembly 230 can include one or more indicators, such as visual indicator 202 configured to indicate alarms and visual indicator 204 configured to indicate status of the pump assembly 230. The visual indicators 202 and 204 can alert a user (for example, patient, health care provider, or the like) to a variety of operating or failure conditions of the pump assembly 230, including alerting the user to normal or proper operating conditions, pump failure, power supplied to the pump or power failure, detection of a leak within the wound cover or flow pathway (sometimes referred to as fluid flow path), suction blockage in the flow pathway, canister full, overpressure, or any other similar or suitable conditions or combinations thereof. Any one or more suitable indicators can be additionally or alternatively used, such as visual, audio, tactile indicator, and so on. The pump assembly 230 can include a display 206 (such as a screen) mounted in a recess formed in a case of the pump assembly 230. The display 206 can be a touch screen display. The display 206 can support playback of audiovisual (AV) content, such as instructional videos, and render a number of screens or graphical user interfaces (GUIs) for configuring, controlling, and monitoring the operation of the pump assembly 230. The pump assembly 230 can include one or more strap mounts 226 for connecting a carry strap to the pump assembly 230 or for attaching a cradle. The canister 220 may be replaced with another canister, such as when the canister 220 has been filled with fluid." and insert
--FIGS. 2A and 2B illustrates a negative pressure wound therapy device 200 (sometimes referred to as a wound therapy device) including a pump assembly 230 and a canister 220. As illustrated, the pump assembly 230 and the canister 220 can be connected, thereby forming the wound therapy device 200. The pump assembly 230 can include one or more indicators, such as visual indicator 202 configured to indicate alarms and visual indicator 204 configured to indicate status of the pump assembly 230. The visual indicators 202 and 204 can alert a user (for example, patient, health care provider, or the like) to a variety of operating or failure conditions of the pump assembly 230, including alerting the user to normal or proper operating conditions, pump failure, power supplied to the pump or power failure, detection of a leak within the wound cover or flow pathway (sometimes referred to as fluid flow path), suction blockage in the flow pathway, canister full, overpressure, or any other similar or suitable conditions or combinations thereof. Any one or more suitable indicators can be additionally or alternatively used, such as visual, audio, tactile indicator, and so on.
The pump assembly 230 can include a display 206 (such as a screen) mounted in a recess formed in a case of the pump assembly 230. The display 206 can be a touch screen display. The display 206 can support playback of audiovisual (AV) content, such as instructional videos, and render a number of screens or graphical user interfaces (GUIs) for configuring, controlling, and monitoring the operation of the pump assembly 230. The pump assembly 230 can include one or more strap mounts 226 for connecting a carry strap to the pump assembly 230 or for attaching a cradle. The canister 220 may be replaced with another canister, such as when the canister 220 has been filled with fluid.--.

In Column 10, Lines 64-67; Column 11, Lines 1-9, delete
"The canister 220 can hold fluid (such as, exudate) removed from the wound cavity 110. The canister 220 includes one or more latches for attaching the canister to the pump assembly 230. For example, the canister 220 as illustrated can have a capacity of 300 mL and include graduations. The canister 220 can include a tubing channel for connecting to the conduit 140. FIG. 2B illustrates a rear view 200B of the pump assembly 230 and the canister 220.
The pump assembly 230 can include a speaker 232 for producing sound. The speaker 232 can generate an acoustic alarm in response to deviations in therapy delivery, non-compliance with therapy delivery, or any other similar or suitable conditions or combinations thereof." and insert
--The canister 220 can hold fluid (such as, exudate) removed from the wound cavity 110.
The canister 220 includes one or more latches for attaching the canister to the pump assembly 230. For example, the canister 220 as illustrated can have a capacity of 300 mL and include graduations. The canister 220 can include a tubing channel for connecting to the conduit 140.
FIG. 2B illustrates a rear view 200B of the pump assembly 230 and the canister 220. The pump assembly 230 can include a speaker 232 for producing sound. The speaker 232 can generate an acoustic alarm in response to deviations in therapy delivery, non-compliance with therapy delivery, or any other similar or suitable conditions or combinations thereof.--.

In Column 11, Lines 17-44, delete
"FIG. 3 illustrates a schematic of a control system 300 which can be employed in the wound monitoring or treatment systems described herein, such as in the wound therapy device 200 of FIGS. 2A and 2B. Electrical components can operate to accept user input, provide output to the user, operate the pressure source, provide network connectivity, and so on. A first processor can be responsible for user activity, and a second processor can be responsible for controlling another device, such as a pump 390. Input and output to the other device, such as a pump 390, one or more sensors (for example, one or more pressure sensors 325 configured to monitor pressure in one or more locations of the fluid flow path), or the like, can be controlled by an input/output (I/O) module 320. For example, the I/O module can receive data from one or more sensors through one or more ports, such as serial (for example, 12C), parallel, hybrid ports, and the like. The processor 310 can receive data from and provide data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, can store data in memory 350 (such as one or more memory modules), which can be internal or external to the processor 310. Any suitable type of memory can be used, including volatile or non-volatile memory, such as RAM, ROM, magnetic memory, solid-state memory, Magnetoresistive random-access memory (MRAM), and the like." and insert
--FIG. 3 illustrates a schematic of a control system 300 which can be employed in the wound monitoring or treatment systems described herein, such as in the wound therapy device 200 of FIGS. 2A and 2B. Electrical components can operate to accept user input, provide output to the user, operate the pressure source, provide network connectivity, and so on. A first processor can be responsible for user activity, and a second processor can be responsible for controlling another device, such as a pump 390.
Input and output to the other device, such as a pump 390, one or more sensors (for example, one or more pressure sensors 325 configured to monitor pressure in one or more locations of the fluid flow path), or the like, can be controlled by an input/output (I/O) module 320. For example, the I/O module can receive data from one or more sensors through one or more ports, such as serial (for example, 12C), parallel, hybrid ports, and the like.
The processor 310 can receive data from and provide data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, can store data in memory 350 (such as one or more memory modules), which can be internal or external to the processor 310. Any suitable type of memory can be used, including volatile or non-volatile memory, such as RAM, ROM, magnetic memory, solid-state memory,

CERTIFICATE OF CORRECTION (continued)
U.S. Pat. No. 12,161,533 B2

Magnetoresistive random-access memory (MRAM), and the like.--.

In Column 15, Lines 13-44, delete
"The dressing information transmitted to the controller 430 by the electronic circuitry 490 can be an identifier that informs the controller 430 of the dressing type being used. Such identifier can be unique to each electronic circuitry 490. The identifier could include parameterized information such as mode of operation (e.g., canister-mode or canisterless-mode), dressing size (e.g., area, capacity, or the like), controlled leak rate (e.g., CLP operational parameters), wound contact layer material (e.g., silicone), etc. The transmitted dressing information can provide functional information, such as the optimum negative pressure to apply to the wound 10 and whether to apply negative pressure to the wound 10 in a continuous or discontinuous fashion. Wound dressing 480 can be configured to be used for a limited duration of time (sometimes referred to as operational lifetime). At the end of the operational lifetime, the wound dressing 480 may need to be replaced. For example, Pico dressing sold by Smith & Nephew can be configured to be worn for 7 days. As another example, Renasys-F foam dressing available from Smith & Nephew can be configured to be worn for 3 days. As yet another example, Renasys-G gauze dressing available from Smith & Nephew can be configured to be worn for 5 days. As yet further example, Acticoat 3 antimicrobial dressing available from Smith & Nephew can be configured to be worn for 3 days, and Acticoat 7 antimicrobial dressing available from Smith & Nephew can be configured to be worn for 7 days. For efficacy of therapy and patient safety, it may be undesirable to exceed the operational lifetime of the dressing. For example, Pico dressing may become saturated with exudate, foam of Renasys-F foam dressing may grow into the wound, or the like." and insert
--The dressing information transmitted to the controller 430 by the electronic
circuitry 490 can be an identifier that informs the controller 430 of the dressing type being used. Such identifier can be unique to each electronic circuitry 490. The identifier could include parameterized information such as mode of operation (e.g., canister-mode or canisterless-mode), dressing size (e.g., area, capacity, or the like), controlled leak rate (e.g., CLP operational parameters), wound contact layer material (e.g., silicone), etc. The transmitted dressing information can provide functional information, such as the optimum negative pressure to apply to the wound 10 and whether to apply negative pressure to the wound 10 in a continuous or discontinuous fashion.
Wound dressing 480 can be configured to be used for a limited duration of time (sometimes referred to as operational lifetime). At the end of the operational lifetime, the wound dressing 480 may need to be replaced. For example, Pico dressing sold by Smith & Nephew can be configured to be worn for 7 days. As another example, Renasys-F foam dressing available from Smith & Nephew can be configured to be worn for 3 days. As yet another example, Renasys-G gauze dressing available from Smith & Nephew can be configured to be worn for 5 days. As yet further example, Acticoat 3 antimicrobial dressing available from Smith & Nephew can be configured to be worn for 3 days, and Acticoat 7 antimicrobial dressing available from Smith & Nephew can be configured to be worn for 7 days. For efficacy of therapy and patient safety, it may be undesirable to exceed the operational lifetime of the dressing. For example, Pico dressing may become saturated with exudate, foam of Renasys-F foam dressing may grow into the wound, or the like.--.

In Column 15, Line 53, delete "that that dressing" and insert --that dressing--.

In Column 16, Lines 32-43, delete
"An indication of the duration of time (or remaining period of time for wearing the dressing)

can be provided by one or more of the electronic circuitry 490 or controller 430. For example, indication can be provided before the operational lifetime has been reached (such as, 1 day before or the like). This could alert the user to an impending dressing change.
Alternatively or additionally, indication can be provided in response to reaching the operational lifetime. Indication can be provided using any of the approaches described herein, such as visually, audibly, and/or tactilely. The dressing 490 and/or the port 410 can include one or more indicators for providing the indication." and insert
--An indication of the duration of time (or remaining period of time for wearing the
dressing) can be provided by one or more of the electronic circuitry 490 or controller 430. For example, indication can be provided before the operational lifetime has been reached (such as, 1 day before or the like). This could alert the user to an impending dressing change. Alternatively or additionally, indication can be provided in response to reaching the operational lifetime. Indication can be provided using any of the approaches described herein, such as visually, audibly, and/or tactilely. The dressing 490 and/or the port 410 can include one or more indicators for providing the indication.--
.

In Column 18, Line 63, delete "is -80mmHg, the" and insert --is -80 mmHg, the--.

In Column 19, Lines 5-37, delete
"In response to a determination that measured pressure satisfies the pressure threshold, it can
be determined that there is loss of negative pressure in a particular fluid flow path (and/or wound) associated with the pressure sensor, which can be indicative of inadequate application of NPWT therapy to the particular wound. Loss of pressure can be due to one or more of blockages, leaks, or the like in the fluid flow path. Such determination of loss of pressure can be made by the controller of the system 500. For example, in response to a determination that pressure measured by the pressure sensor of the electronic circuitry 590A meets or falls below the pressure threshold, it can be determined that there is loss of negative pressure at the wound 10A, which can be indicative of inadequate application of NPWT therapy to the wound 10B.
Additionally or alternatively, in response to a determination that pressure measured by the pressure sensor of the electronic circuitry 590B meets or falls below the pressure threshold (or a different pressure threshold), it can be determined that there is loss of negative pressure at the wound 10B, which is indicative of inadequate application of NPWT therapy to the wound 10B. In some cases, any one or more of the pressure sensors can be paired with the controller. This can allow the controller to identify for which of the fluid flow paths (and/or wounds) pressure measurements are being provided. Pairing and/or monitoring of a wound can be performed, for example, via Bluetooth, Zigbee, or the like. In some cases, in addition to or instead of pairing, one or more pressure sensors can transmit an identifier configured to identify associated fluid flow path (and/or wound). For example, the identifier can be a dressing identifier as described herein. The identifier can be unique to each of the pressure sensors (or electronic circuitries)." and insert
--In response to a determination that measured pressure satisfies the pressure threshold, it
can be determined that there is loss of negative pressure in a particular fluid flow path (and/or wound) associated with the pressure sensor, which can be indicative of inadequate application of NPWT therapy to the particular wound. Loss of pressure can be due to one or more of blockages, leaks, or the like in the fluid flow path. Such determination of loss of pressure can be made by the controller of the system 500. For example, in response to a determination that pressure measured by the pressure sensor of the electronic circuitry 590A meets or falls below the pressure threshold, it can be determined that there is loss of negative pressure at the wound 10A, which can be indicative of inadequate application of NPWT therapy to the wound 10B. Additionally or alternatively, in response to a determination that pressure measured by the pressure sensor of the electronic circuitry 590B meets or falls below the pressure threshold (or a different pressure threshold), it can be determined that there is loss of negative pressure at the wound 10B, which is indicative of inadequate application of NPWT therapy to the wound 10B. In some cases, any one or more of the pressure sensors can be paired with the controller. This can allow the controller to identify for which of the fluid flow paths (and/or wounds) pressure measurements are being provided. Pairing and/or monitoring of a wound can be performed, for example, via Bluetooth, Zigbee, or the like. In some cases, in addition to or instead of pairing, one or more pressure sensors can transmit an identifier configured to identify associated fluid flow path (and/or wound). For example, the identifier can be a dressing identifier as described herein. The identifier can be unique to each of the pressure sensors (or electronic circuitries).--.

In the Claims

In Column 22, Claim 1, Line 34, delete "wound dressing;" and insert --wound dressing:--.

In Column 24, Claim 14, Line 8, delete "first or second wound" and insert --first wound--.

In Column 24, Claim 14, Line 14, delete "with other a" and insert --with a--.